United States Patent

Hirata et al.

Patent Number: 5,708,185
Date of Patent: Jan. 13, 1998

[54] PROCESS FOR PRODUCING 1-HYDROXYTHIENOIMIDAZOLE CARBOXYLIC ACID AND THIENOIMIDAZOLE CARBOXYLIC ACID

[75] Inventors: Norihiko Hirata; Yasunobu Miyamoto; Masahiko Mizuno; Toshiya Takahashi, all of Osaka, Japan

[73] Assignee: Sumitomo Chemical Company, Limited, Osaka, Japan

[21] Appl. No.: 773,354

[22] Filed: Dec. 26, 1996

[30] Foreign Application Priority Data

Dec. 26, 1995 [JP] Japan .................. 7-338632
Dec. 26, 1995 [JP] Japan .................. 7-338636

[51] Int. Cl.⁶ ........................... C07D 495/04
[52] U.S. Cl. ........................... 548/303.7
[58] Field of Search ................... 548/303.7

[56] References Cited

U.S. PATENT DOCUMENTS 3,740,416  6/1973  Gerecke et al. .

FOREIGN PATENT DOCUMENTS 61-151194  7/1986  Japan .

*Primary Examiner*—Patricia L. Morris
*Attorney, Agent, or Firm*—Sughrue, Mion, Zinn, Macpeak & Seas, PLLC

[57] ABSTRACT

A process for producing 1-hydroxythienoimidazole carboxylic acid represented by formula (2):

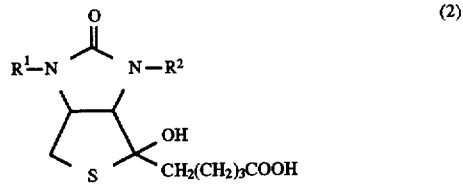

(2)

wherein $R^1$ and $R^2$ are as defined in the specification; wherein said process comprises the steps of:

(a) reacting thienoimidazole represented by formula (1) with 1,4-dihalogenodimagnesium butane, in the presence of tetrahydrofuran or a mixed solvent comprising tetrahydrofuran and an aromatic solvent to produce a reaction mixture:

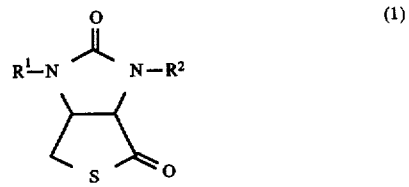

(1)

wherein $R^1$ and $R^2$ are as defined above;

(b) adding the reaction mixture obtained in said step (a) and, optionally, carbon dioxide, to: (i) a solution comprising carbon dioxide and tetrahydrofuran, or (ii) a solution comprising carbon dioxide, tetrahydrofuran and an dramatic solvent to give a reaction liquid; and (c) hydrolyzing said reaction liquid.

16 Claims, No Drawings

PROCESS FOR PRODUCING 1-HYDROXYTHIENOIMIDAZOLE CARBOXYLIC ACID AND THIENOIMIDAZOLE CARBOXYLIC ACID

FIELD OF THE INVENTION

The present invention relates to a process for producing 1-hydroxythienoimidazole carboxylic acid and thienoimidazole carboxylic acid. More particularly, the present invention relates to a process for producing 1-hydroxythienoimidazole carboxylic acid (represented by formula (2) below) and thienoimidazole carboxylic acid (represented by formula (3) below) which are useful as intermediates for the production of biotin (vitamin H).

BACKGROUND OF THE INVENTION

Hitherto, there has been known a process for producing 1-hydroxythienoimidazole carboxylic acid involving the reaction of 4,6-dibenzyl-1,5-dioxohexahydro-1H-thieno[3,4-d]imidazole with 1,4-dihalogenodimagnesium butane, followed by reacting carbon dioxide (Japanese Patent Publication (Kokai) No.61-151194).

However, as the above process involves the formation of a large amount of byproducts, the yield of 1-hydroxythienoimidazole carboxylic acid is low.

As a result, from an industrial perspective, the above process is not ideal.

SUMMARY OF THE INVENTION

An object of the present invention is to provide a process for producing 1-hydroxythienoimidazole carboxylic acid (2) in good yield and with industrial advantage.

The process of this invention is the result of extensive studies relating to solving the problems of, for example, insufficient yield from an industrial perspective.

Accordingly, the first process of the present invention (referred to herein as "Process A") produces 1-hydroxythienoimidazole carboxylic acid represented by formula (2):

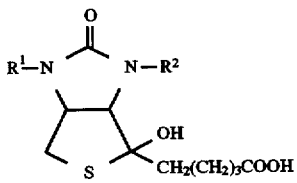

wherein $R^1$ and $R^2$ are each selected from the group consisting of a aralkyl group and an allyl group, wherein the aralkyl group and the allyl group are unsubstituted or substituted by one member selected from the group consisting of an alkyl group, alkoxyl group, nitro group, and halogen atom; wherein the process comprises the steps of:

(a) reacting a thienoimidazole represented by formula (1) with 1,4-dihalogenodimagnesium butane, in the presence of tetrahydrofuran or a mixed solvent comprising tetrahydrofuran and aromatic solvent to produce a reaction mixture,:

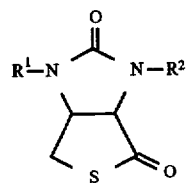

wherein $R^1$ and $R^2$ are as defined above;

(b) adding the reaction mixture obtained in step (a) and, optionally, carbon dioxide, to: (i) a solution comprising carbon dioxide and tetrahydrofuran, or (ii) a solution comprising carbon dioxide, tetrahydrofuran and aromatic solvent to give reaction liquid; and (c) hydrolyzing the reaction liquid.

The second process of the present invention (referred to herein as "Process B") produces 1-hydroxythienoimidazole carboxylic acid represented by formula (2):

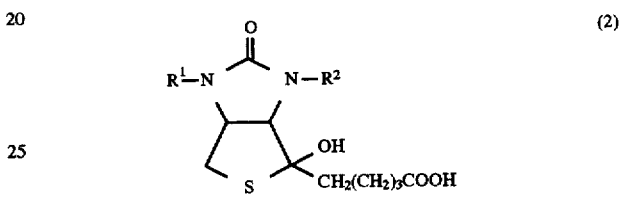

wherein $R^1$ and $R^2$ are as defined above; wherein the process comprises the steps of:

(a) reacting a thienoimidazole represented by formula (1) with 1,4-dihalogenodimagnesium butane, in the presence of tetrahydrofuran or a mixed solvent comprising tetrahydrofuran and an arctic solvent to produce a reaction mixture,:

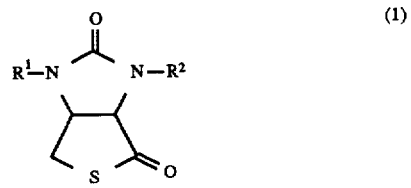

wherein $R^1$ and $R^2$ are as defined above; and wherein the thienoimidazole represented by formula (1) is added to the 1,4-dihalogenodimagnesium butane either solely or in cake state or slurry state, wherein the cake state and slurry state are made by adding a small amount of either tetrahydrofuran or a mixed solvent comprising tetrahydrofuran and an aromatic solvent;

(b) reacting the reaction mixture obtained in step (a) with carbon dioxide to produce a reaction liquid; and (c) hydrolyzing the reaction liquid.

Finally, the present invention is also directed to processes of producing thienoimidazole carboxylic acid represented by formula (3):

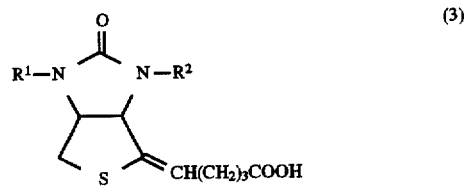

wherein $R^1$ and $R^2$ are as defined above. These processes include using the processes of Process A and Process B, wherein the thienoimidazole carboxylic acid represented by formula (3) is obtained through 1-hydroxythienoimidazole carboxylic acid represented by formula (2).

DETAILED DESCRIPTION

The present invention is hereinafter described in detail.

The thienoimidazole represented by formula (1), which is used in both Processes A and B as a starting material, may be either optically active or racemic, and can be obtained, for example, by a method as described in Japanese Patent Publication (Kokoku) No. 53-27279.

The protective group $R^1$ and $R^2$, which are used in the thienoimidazole represented by (1) to produce the 1-hydroxythienoimidazole carboxylic acid represented by formula (2) and the thienoimidazole carboxylic acid represented by formula (3), may each be an aralkyl group or an allyl group. The aralkyl group may contain from 7 to 20 carbon atoms, and each of the aralkyl group and allyl group may be unsubstituted or substituted with at least one alkyl group, alkoxyl group, nitro group, or halogen atom. Alkyl and alkoxy groups in this specification including the accompanying claims are straight or branched chain and generally contain from 1 to 6, preferably 1 to 4 carbon atoms.

Preferred examples of the unsubstituted or substituted aralkyl group are a benzyl group, α-methylbenzyl group, p-methoxybenzyl group, p-nitrobenzyl group, p-bromobenzyl group, p-chlorobenzyl group, p-methylbenzyl group, naphtylmethyl group, triphenylmethyl group. The benzyl group is particularly preferred. In addition, preferred exiles of the unsubstituted or substituted allyl group are allyl group, 2-butenyl group and 3-methyl-2-butenyl group.

The solution of 1,4-dihalogenodimagnesium butane in tetrahydrofuran or in a mixed solvent of tetrahydrofuran and aromatic solvent can be prepared by an ordinary Grignard reagent preparing method, for example, by reacting an approximately 0.5 mole of dihalogenobutane, such as 1,4-dichlorobutane and 1,4-dibromobutane, with 1 mole of metal magnesium in tetrahydrofuran or a mixed solvent of tetrahydrofuran and an aromatic solvent.

In the present invention, the use of tetrahydrofuran or the use of a mixed solvent of tetrahydrofuran and an aromatic solvent in both Process A and Process B are collectively referred to as "reaction solvent".

When using an aromatic solvent in the reaction solvent of both Process A and B, the weight ratio of the aromatic solvent to tetrahydrofuran is generally in the range of 0.01 to 0.5, preferably 0.02 to 0.25. Examples of the aromatic solvents which can be used in the reaction solvent of Process A and Process B include: benzene; alkylbenzenes such as toluene, o-xylene, m-xylene, p-xylene, mixed xylene, ethylbenzene, cumene, cymene and trimethylbenzene; alkoxybenzenes such as anisole; and the like. Of these, benzene, toluene, p-xylene, o-xylene, m-xylene are mixed in both Process A and Process B.

PROCESS A

Production of 1-Hydroxythienoimidazole Carboxylic Acid Represented by Formula (2)

Thienoimidazole represented by formula (1) is added to a solution of (i) 1,4-dihalogenodimagnesium butane in (ii) the aforementioned reaction solvent to produce a reaction mixture. Optionally, a tertiary amine is added to the solution of 1,4-dihalogenodimagnesium butane in the aforementioned reaction solvent. Next, the reaction mixture and, optionally, carbon dioxide, are added to: (i) a solution comprising carbon dioxide and tetrahydrofuran, or (ii) a solution comprising carbon dioxide, tetrahydrofuran and an aromatic solvent to produce a reaction liquid. Finally, the 1-hydroxythienoimidazole carboxylic acid represented by formula (2) is produced by hydrolyzing the resulting reaction liquid with, for example, water or an aqueous solution such as aqueous ammonium chloride.

Preferably, the addition of thienoimidazole represented by formula (1) is made by adding such directly to the solution of 1,4-dihalogenodimagnesium butane, or by adding such in a cake state or slurry state. The cake state and slurry state are prepared by adding a small amount of reaction solvent to the thienoimidazole represented by formula (1). Preferably, an industrially advantageous yield is achieved when the thienoimidazole represented by formula (1) is directly added to the solution of 1,4-dihalogenodimagnesium butane in reaction solvent. The amount to be used for the cake and slurry state of the thienoimidazole represented by formula (1) is generally no more than 10 times by weight, preferably, no more than 7 times by weight, based on the amount of the thienoimidazole represented by formula (1).

Preferred examples of the tertiary amines which may be added to the solution containing the 1,4-dihalogenodimagnesium butane are as follows: trialkyl amines such as triethylamine; N,N,N',N'-alkyl substituted alkylenediamines such as N,N,N',N'-tetramethylethylenediamine, N,N,N',N'-tetraethylethylenediamine, N,N,N',N'-tetramethyl-1,3-propanediamine; and dialkylamino aromatic compounds such as N,N-dimethylaniline, 1,8-bis(dimethylamino) naphthalene, and the like. Especially preferred is the use of N,N,N',N'-tetramethylethylenediamine.

When the tertiary amine is used, the amount of the tertiary amine is generally 0.0001 to 10 mole equivalents, preferably 0.01 to 2 mole equivalents, based on the amount of the thienoimidazole represented by (1).

The amount of reaction solvent to be used in this reaction is normally 3 to 50 times by weight, preferably 8 to 20 times by weight, more preferably 10 to 15 times by weight, based on the amount of the thienoimidazole represented by formula (1).

The addition time for the thienoimidazole represented by formula (1) to the solution of 1,4-dihalogenodimagnesium butane is generally about 0.1 to 10 hours. The reaction temperature is generally −78° to 10° C., preferably, −50° to −20° C.

After the addition of thienoimidazole represented by formula (1), the reaction mixture may be stirring for some time before such is subjected to the reaction with carbon dioxide. Generally, however, the reaction mixture is promptly subjected to the reaction with carbon dioxide.

After the reaction mixture is prepared, such is added to either: (i) a solution comprising carbon dioxide and tetrahydrofuran; or (ii) a solution comprising carbon dioxide, tetrahydrofuran and an aromatic solvent (examples include those set forth hereinabove) to give a reaction liquid. The amount of either the tetrahydrofuran or total amount of tetrahydrofuran and aromatic solvent is generally 0.1 to 20 times, preferably, 1 to 10 times, more preferably, 2 to 4 times by weight, based on the weight of the thienoimidazole represented by formula (1).

Optionally, carbon dioxide may separately be added to the above solutions of: (i) carbon dioxide and tetrahydrofuran; or (ii) carbon dioxide, tetrahydrofuran and an aromatic solvent. The carbon dioxide is added to the above solutions by separately blowing carbon dioxide gas into the above solutions while dropwise adding the reaction mixture.

The total amount of the carbon dioxide to be used is generally 1 to 20 equivalents, preferably, 3 to 8 equivalents, based on the amount of the thienoimidazole represented by formula (1). The concentration of carbon dioxide dissolved in the carbon dioxide solution is generally not less than 0.001 kg, preferably, not less than 0.01 kg, more preferably not less than 0.04 kg, based on 1 Kg of either the tetrahydrofuran or the combination of tetrahydrofuran and aromatic solvent. The upper limit of carbon dioxide is determined by that amount of carbon dioxide necessary to prepare a saturated carbon dioxide/tetrahydrofuran solution or a saturated carbon dioxide/tetrahydrofuran/aromatic solvent solution. From the viewpoint of simplification, it is preferred to dissolve the amount of carbon dioxide (in either tetrahydrofuran or tetrahydrofuran and aromatic solvent) necessary to produce a saturated carbon dioxide solution.

Dissolution of carbon dioxide in either tetrahydrofuran or the combination of tetrahydrofuran and aromatic solvent is accomplished by, for example, blowing carbon dioxide gas into the tetrahydrofuran or into the combination of the tetrahydrofuran and aromatic solvent.

The reaction temperature between the reaction mixture and the carbon dioxide (in the carbon dioxide solution) is generally in the range of $-78°$ to $10°$ C., preferably $-50°$ to $-20°$ C. and the reaction time is generally about 0.1 to 5 hours. If necessary, stirring of the reaction mixture during the addition can be maintained.

After the reaction, the reaction liquid is hydrolyzed to give 1-hydroxythienoimidazole carboxylic acid represented by formula (2). This may be accomplished by adding the reaction liquid to water or an aqueous solution such as aqueous ammonium chloride.

1-Hydroxythienoimidazole carboxylic acid represented by formula (2) can be isolated by carrying out ordinary after-treatments such as phase separation, concentration and purification by column chromatography. Alternatively, without isolation, the reaction liquid before hydrolyzation may be directly utilized in the production of thienoimidazole carboxylic acid represented by formula (3).

PROCESS B

Production of 1-Hydroxythienoimidazole Carboxylic Acid Represented by Formula (2)

Thienoimidazole represented by formula (1) is added to a solution of (1) 1,4-dihalogenodimagnesium butane in (ii) the aforementioned reaction solvent to produce a reaction mixture. The addition of thienoimidazole represented by formula (1) is made either directly, or in a cake state or slurry state by adding a small amount of the aforementioned reaction solvent. Next, the reaction mixture is reacted with carbon dioxide to give a reaction liquid, followed by hydrolyzing the reaction liquid with, for example, water or an aqueous solution such as aqueous ammonium chloride to give 1-hydroxythienoimidazole carboxylic acid represented by formula (2).

As in Process A, the cake state and slurry state of the thienoimidazole represented by formula (1) are prepared by adding a small amount of the aforementioned reaction solvent to the thienoimidazole represented by formula (1). The amount of reaction solvent to be used for the cake or slurry of thienoimidazole represented by formula (1) is generally no more than 10 times by weight, preferably, no more than 7 times weight, based on the weight of thienoimidazole represented by formula (1). Preferably, an industrially advantageous yield is achieved when the thienoimidazole represented by formula (1) is directly added to the solution of 1,4-dihalogenodimagnesium butane in reaction solvent.

Optionally, a tertiary amine may be added to the solution of 1,4-dihalogenodimagnesium butane in the aforementioned reaction solvent. The kind and the amount of the tertiary amines used in this process are the same as those of Process A.

The amount and kind of aromatic solvents to be used in the process are the same as set forth above.

The amount of reaction solvent to be used in this reaction is the same as the amount used in Process A.

Reaction conditions such as the addition time of thienoimidazole represented by formula (1), reaction temperature, and the like are same as those of Process A.

After the addition of thienoimidazole (1), as in Process A, the reaction mixture may be stirred for some time before such is subjected to the reaction with carbon dioxide. Generally, however, the reaction mixture is promptly subjected to the reaction with carbon dioxide.

The amount of carbon dioxide to be used in the reaction between the reaction mixture and carbon dioxide is generally 1 to 20 mole equivalents, preferably 3 to 8 mole equivalents, based on the amount of the thienoimidazole represented by formula (1).

The reaction between the reaction mixture and carbon dioxide may be carried out by separately adding the reaction mixture and carbon dioxide into the aforementioned reaction solvent; adding carbon dioxide directly into the reaction mixture; the method shown in Process A; and the like. From the perspective of yield and industrial production, it is noted that the method of Process A is preferred.

In the reaction between the reaction mixture and carbon dioxide, additional reaction solvent can be used, and the amount thereof is generally 0.1 to 20 times by weight, preferably, 1 to 10 times by weight, more preferably, 2 to 4 times by weight, based on the weight of thienoimidazole represented by formula (1).

The reaction temperature is the same as that shown in Process A.

The reaction between the contents of the reaction mixture carbon dioxide is generally conducted over a time period of about 0.1 to 5 hours. If necessary or desirable, stirring of the reaction mixture may be maintained during this reaction.

After the reaction, the reaction liquid is hydrolyzed to give 1-hydroxythienoimidazole carboxylic acid represented by formula (2). As in Process A, this my be accomplished by adding the reaction liquid to water or an aqueous solution such as aqueous ammonium chloride.

1-Hydroxythienoimidazole carboxylic acid represented by (2) can be isolated by carrying out ordinary after-treatments such as phase separation, concentration and purification by column chromatography. Alternatively, without isolation, the reaction liquid before hydrolyzation may be directly utilized in the production of thienoimidazole carboxylic acid represented by formula (3).

Production of Thienoimidazole Carboxylic Acid Represented by Formula (3)

Thienoimidazole carboxylic acid represented by formula (3) can generally be obtained by dehydrating 1-hydroxythienoimidazole carboxylic acid represented by formula (2) or by hydrolyzing and dehydrating the aforementioned reaction liquid obtained in Process A or B.

When the aforementioned reaction liquid obtained in Process A or B is used for the reaction, co-existence of proton donor such as water, acid and alcohols, is necessary because of the necessity of hydrolyzation of the reaction liquid prior to dehydration reaction. The amount of proton donor such as water, acid and alcohol is generally 0.1 to 50 times by weight, preferably, 1 to 20 time by weight, more preferably 5 to 10 times by weight, based on the weight of thienoimidazole represented by formula (1).

The solvents which can be used in the process may be those referred to hereinabove as the reaction solvent, and aromatic solvents (e.g., xylene, toluene, benzene, and the like). The amount of the solvent is generally 0 to 50 times by weight, preferably, 2 to 20 time by weight, more preferably, 5 to 10 times by weight, based on the weight of thienoimidazole represented by formula (1).

Generally, an acidic catalyst is used in the dehydration reaction. As the acidic catalyst, conventional inorganic acid and organic acid may be used. Examples of the acidic catalyst are sulfuric acid, hydrochloric acid, acetic acid, phosphoric acid, hydrogen bromide, p-toluenesulfonic acid, benzene sulfonic acid and methane sulfonic acid. The amount of the acidic catalyst is generally 0.01 to 6 equivalents, preferably, 0.02 to 0.3 equivalent, based on the weight of 1-hydroxythienoimidazole carboxylic acid represented by formula (2). The reaction temperature is generally 10° to 120° C., preferably 20° to 100° C. It is advantageous to carry out the reaction while removing water through azeotropic distillation.

Completion of the reaction can be confirmed, for example, by liquid chromatography, thin layer chromatography, and the like.

After the reaction, thienoimidazole carboxylic acid represented by formula (3) can be obtained by conventional after-treatments, for example, extracting by aqueous alkali, followed by extracting by organic solvent in neutral or acidic state.

If necessary or desired, thienoimidazole carboxylic acid represented by formula (3) may be purified, for example, by recrystallization, column chromatography, and the like.

The thienoimidazole carboxylic acid represented by formula (3) can easily be converted into biotin by reduction and then deprotection under acidic conditions in accordance with the methods as described, for example, in Japanese Patent Publication (Kokai) No. 61-151194 or Japanese Patent Publication (Kokoku) No. 63-8954 (=U.S. Pat. No. 4,537,973).

1-Hydroxythienoimidazole carboxylic acid represented by formula (2) and thienoimidazole carboxylic acid represented by formula (3) are useful as the intermediates for biotin. According to the present invention, such can be produced in high yield and with industrial advantage.

Examples of the present invention are provided below. However, the present invention is not to be limited by these examples. Unless otherwise indicated, all parts, percentages, and the like, are by weight.

EXAMPLE 1

To a suspension of 6.9 g of magnesium and 80 g of tetrahydrofuran, 3 g of 1,4-dichlorobutane, and then a solution comprising 0.1 g of iodine and 2 g of tetrahydrofuran were dropwise added at 50° C. 65 g of tetrahydrofuran was added to the resulting solution, and then 14.2 g of 1,4-dichlorobutane was added while refluxing for 30 minutes. After completion of the addition, the mixture was stirred at 60°–65° C. for 3 hours. The solution was dropwise added to the solution comprising 20 g of tetrahydrofuran and 23 g of toluene, which was cooled to −25°—−20° C. at the same temperature in 0.5 hours, after which 25.4 g of (3aS, 6aR)-4,6-dibenzyl-1,5-dioxohexahydro-1H-thieno[3,4-d]imidazole was added thereto at a liquid temperature of −35° C. in 0.5 hour. The resulting mixture was dropwise added to 85 g of a solution of tetrahydrofuran (cooled to −25° to −5° C.) in which carbon dioxide gas (1.5 equivalents to (3aS, 6aR)-4,6-dibenzyl-1,5-dioxohexahydro-1H-thieno[3,4-d] imidazole) was previously blown and dissolved thereto, simultaneously with the blowing in of carbon dioxide gas (3.5 equivalents) at the same temperature in an hour. The resulting reaction liquid was dropwise added to 15% sulfuric acid, incorporated with 28 g of toluene, and the mixture was stirred for 1 hour, followed by separating the aqueous layer. The organic layer was incorporated with 160 g of toluene, and concentrated under reduced pressure. The residue was incorporated with 5% sodium hydroxide, stirred, and the mixture was phase-separated, after which toluene was added to the aqueous layer, which was adjusted to pH 6.5 with 30% sulfuric acid, and then phase-separated. The organic layer was concentrated to give 5-((3aS,6aR)-4,6-dibenzyl-5-oxohexahydro-1H-thieno[3,4-d]imidazole-1-ylidene) pentanoic acid as an oily substance. Calculating the net yield of pure 5-((3aS,6aR)-4,6-dibenzyl-5-oxohexahydro-1H-thieno[3,4-d]imidazole-1-ylidene)pentanoic acid using liquid chromatography, we found that it was 29.5 g.

The resulting compound was recrystallized with 2-propanol and hexane to show the physical properties of 84°–85° C. of melting point; $[\alpha]D^{20}=236.2°$ (C=1.0, methanol).

EXAMPLE 2

In the same manner as in Example 1 except that the temperature in the addition of (3aS, 6aR)-4,6-dibenzyl-1,5-dioxohexahydro-1H-thieno[3,4-d]imidazole was set at −25° C., the reaction and after-treatment were carried out to obtain 5-((3aS,6aR)-4,6-dibenzyl-5-oxohexahydro-1H-thieno[3,4-d]imidazole-1-ylidene)pentanoic acid as an oily substance. Calculating the net yield of pure 5-((3aS,6aR)-4,6-dibenzyl-5-oxohexahydro-1H-thieno[3,4-d]imidazole-1-ylidene)pentanoic acid using liquid chromatography, we found that it was 28.5 g.

EXAMPLE 3

In the same manner as in Example 1 except that the temperature in the addition of (3aS, 6aR)-4,6-dibenzyl-1,5-dioxohexahydro-1H-thieno[3,4-d]imidazole is set at −45° C., the reaction and after-treatment are carried out to obtain 5-((3aS,6aR)-4,6-dibenzyl-5-oxohexahydro-1H-thieno[3,4-d]imidazole-1-ylidene)pentanoic acid as an oily substance.

EXAMPLE 4

To a suspension of 6.9 g of magnesium and 80 g of tetrahydrofuran, 3 g of 1,4-dichlorobutane, and then a solution comprising 0.1 g of iodine and 2 g of tetrahydrofuran were dropwise added at 50° C. 65 g of tetrahydrofuran was added to the resulting solution, and then 14.2 g of 1,4-dichlorobutane was dropwise added while refluxing for 30 minutes. After completion of the addition, the mixture was stirred at 60° to 65° C. for 3 hours. The solution was dropwise added to the solution comprising 20 g of tetrahydrofuran and 23 g of toluene, which was cooled to −25°—−20° C., at the same temperature in 0.5 hour, after which 25.4 g of (3aS, 6aR)-4,6-dibenzyl-1,5-dioxohexahydro-1H-thieno[3,4-d]imidazole was added thereto at a liquid temperature of −35° C. in 0.5 hours. Thereafter, carbon dioxide gas (6 equivalents to (3aS, 6aR)-4,6-dibenzyl-1,5-dioxohexahydro-1H-thieno[3,4-d]imidazole) was introduced in an hour. The reaction liquid was poured into 15% sulfuric acid, incorporated with 28 g of toluene, and the mixture was stirred for an hour, followed by separating the aqueous layer. The organic layer was incorporated with 160 g of toluene and concentrated under reduced pressure. The residue was incorporated with 5% sodium hydroxide, and the mixture was stirred and phase-separated, after which toluene was added to the aqueous layer, which was adjusted to pH 6.5 with 30% sulfuric acid, and the liquid was phase-separated. The organic layer was concentrated to obtain 5-((3aS,6aR)-4,6-dibenzyl-5-oxohexahydro-1H-thieno[3,4-d]imidazole-1-ylidene)pentanoic acid as an oily substance. Calculating the net yield of pure 5-((3aS,6aR)-4,6-dibenzyl-5-oxohexahydro-1H-thieno[3,4-d]imidazole-1-ylidene)pentanoic acid using liquid chromatography, we found that it was 28.5 g.

The resulting compound was recrystallized with 2-propanol and hexane to show the physical properties of 84°–85° C. of melting point; $[\alpha]D^{20}=236.2°$ (C=1.0, methanol).

EXAMPLE 5

In the same manner as in Example 4, 1,4-dichlorodimagnesium butane was prepared, to which 90 g of tetrahydrofuran was added, and the mixture was cooled to −35° C. To the mixture, a slurry comprising 25.4 g of (3aS, 6aR)-4,6-dibenzyl-1,5-dioxohexahydro-1H-thieno[3,4-d] imidazole and 120 g of tetrahydrofuran cooled to −30° C. was dropwise added while the temperature in the reactor was kept at −35° C. over 0.5 hour. Thereafter, the reaction and after-treatments were carried out in the same manner as in Example 1 to obtain 5-((3aS,6aR)-4,6-dibenzyl-5-oxohexahydro-1H-thieno[3,4-d]imidazole-1-ylidene) pentanoic acid as an oily substance. Calculating the net yield of pure 5-((3aS,6aR)-4,6-dibenzyl-5-oxohexahydro-1H-thieno[3,4-d]imidazole-1-ylidene)pentanoic acid using liquid chromatography, we found that it was 28.5 g.

EXAMPLE 6

To a suspension of 6.9 g of magnesium and 80 g of tetrahydrofuran, 3 g of 1,4-dichlorobutane, and then a solution comprising 0.1 g of iodine and 2 g of tetrahydrofuran were dropwise added at 50° C. 65 g of tetrahydrofuran was added to the resulting solution, and then 14.2 g of 1,4-dichlorobutane was dropwise added while refluxing for 30 minutes. After completion of the addition, the mixture was stirred at 60°–65° C. for 3 hours. The solution was dropwise added to the solution comprising 20 g of tetrahydrofuran and 23 g of toluene which was cooled to −25°—20° C. at the same temperature in 0.5 hours, after which 25.4 g of (3aS, 6aR)-4,6-dibenzyl-1,5-dioxohexahydro-1H-thieno[3,4-d] imidazole was added thereto at a liquid temperature of −35° C. in 0.5 hours. The resulting mixture was dropwise added to 85 g of a solution of tetrahydrofuran cooled to −25° to −5° C. in which carbon dioxide gas (1.5 equivalents to (3aS, 6aR)-4,6-dibenzyl-1,5-dioxohexahydro-1H-thieno[3,4-d] imidazole) was previously blown and dissolved thereinto, simultaneously with the blowing in of carbon dioxide gas (3.5 equivalents) at the same temperature in an hour.

The reaction mixture was poured into water, incorporated with 28 g of toluene, and the mixture was stirred for 1 hour, followed by separating the aqueous layer. The organic layer was concentrated to obtain 5-(4,6-dibenzyl-1-hydroxy-5-oxohexahydro-1H-thieno[3,4-d]imidazol-1-yl)pentanoic acid as an oily substance. Calculating the net yield of pure 5-(4,6-dibenzyl-1-hydroxy-5-oxohexahydro-1H-thieno[3,4-d]imidazol-1-yl)pentanoic acid using liquid chromatography, we found that it was 30.8 g.

While the invention has been described in detail and with reference to specific embodiments thereof, it will be apparent to one skilled in the art that various changes and modifications can be made without departing from the spirit and scope thereof.

What is claimed is:

1. A process for producing 1-hydroxythienoimidazole carboxylic acid represented by formula (2):

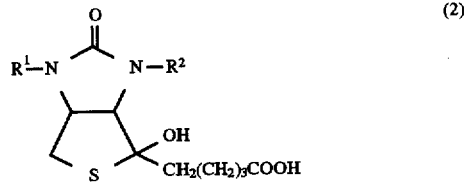

wherein $R^1$ and $R^2$ are each selected from the group consisting of an aralkyl group and allyl group, wherein said aralkyl group and allyl group are unsubstituted or substituted by one member selected from the group consisting of an alkyl group, alkoxyl group, nitro group, and halogen atom; wherein said process comprises the steps of:

(a) reacting thienoimidazole represented by formula (1) with 1,4-dihalogenodimagnesium butane, in the presence of tetrahydrofuran or a mixed solvent comprising tetrahydrofuran and an aromatic solvent to produce a reaction mixture:

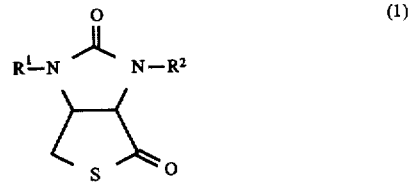

wherein $R^1$ and $R^2$ are as defined above;

(b) adding the reaction mixture obtained in said step (a) and, optionally, carbon dioxide, to: (i) a solution comprising carbon dioxide and tetrahydrofuran, or (ii) a solution comprising carbon dioxide, tetrahydrofuran and an aromatic solvent to give a reaction liquid; and (c) hydrolyzing said reaction liquid.

2. The process according to claim 1, wherein the step (a) is carried out further in the presence of a tertiary amine.

3. The process according to claim 1, wherein said aromatic solvent in step (a) and said aromatic solvent in step (b) are selected from the group consisting of benzene, toluene, o-xylene, m-xylene, p-xylene and mixed xylene.

4. The process according to claim 2, wherein said tertiary amine is N,N,N',N'-tetramethylethylenediamine.

5. The process according to claim 1, wherein said solution comprising carbon dioxide and tetrahydrofuran and said solution comprising carbon dioxide, tetrahydrofuran and aromatic solvent are saturated with carbon dioxide.

6. The process according to claim 1, wherein thienoimidazole represented by formula (1) is added to the reaction in step (a) either directly or in a cake state or slurry state, wherein said cake state and slurry state are made by adding a small amount of either tetrahydrofuran or a mixed solvent comprising tetrahydrofuran and an aromatic solvent.

7. A process for producing 1-hydroxythieno carboxylic acid represented by formula (2):

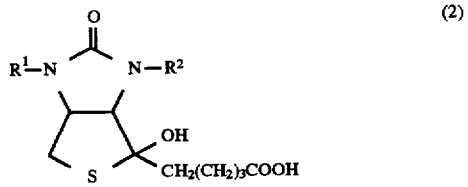

wherein $R^1$ and $R^2$ are each selected from the group consisting of an aralkyl group and allyl group, wherein said aralkyl group and allyl group are unsubstituted or substituted by one member selected from the group consisting of an alkyl group, alkoxyl group, nitro group, and halogen atom; wherein said process comprises the steps of:

(a) reacting a thienoimidazole represented by formula (1) with 1,4-dihalogenodimagnesium butane, in the presence of tetrahydrofuran or a mixed solvent comprising tetrahydrofuran and an aromatic solvent to produce a reaction mixture:

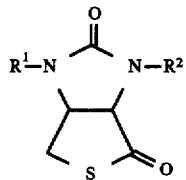
(1)

wherein $R^1$ and $R^2$ are as defined above; and wherein said thienoimidazole represented by formula (1) is added to said 1,4-dihalogenodimagnesium butane either directly or in a cake state or slurry state, wherein said cake state and slurry state are made by adding a small amount of either tetrahydrofuran or a mixed solvent comprising tetrahydrofuran and an aromatic solvent;

(b) reacting said reaction mixture obtained in step (a) with carbon dioxide to produce a reaction liquid; and
(c) hydrolyzing said reaction liquid.

8. The process according to claim 7, wherein said step (a) is carried out in the presence of a tertiary amine.

9. The process according to claim 7, wherein said aromatic solvent in said step (a) between said thienoimidazole represented by formula (1) and 1,4-dihalogenodimagnesium butane and used in the mixed solvent to form said thienoimidazole represented by formula (1) in the cake or slurry state, is selected from the group consisting of benzene, toluene, o-xylene, m-xylene, p-xylene and mixed xylene.

10. The process according to claim 8, wherein said tertiary amine is N,N,N',N'-tetramethylethylenediamine.

11. A process for producing thienoimidazole carboxylic acid represented by formula (3):

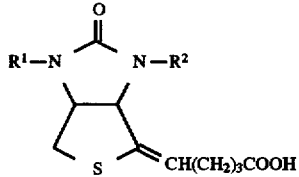
(3)

wherein $R^1$ and $R^2$ are each selected from the group consisting of an aralkyl group and allyl group, wherein said aralkyl group and allyl group are unsubstituted or substituted by one member selected from the group consisting of an alkyl group, alkoxyl group, nitro group, and halogen atom; wherein said process comprises the steps of:

(a) reacting thienoimidazole represented by formula (1) with 1,4-dihalogenodimagnesium butane, in the presence of tetrahydrofuran or a mixed solvent comprising tetrahydrofuran and an aromatic solvent to produce a reaction mixture:

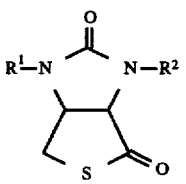
(1)

wherein $R^1$ and $R^2$ are as defined above;
(b) adding the reaction mixture obtained in said step (a) and, optionally, carbon dioxide, to: (i) a solution comprising carbon dioxide and tetrahydrofuran, or (ii) a solution comprising carbon dioxide, tetrahydrofuran and an aromatic solvent to give a reaction liquid; and (c) hydrolyzing and dehydrating said reaction liquid.

12. A process for producing thienoimidazole carboxylic acid represented by formula (3):

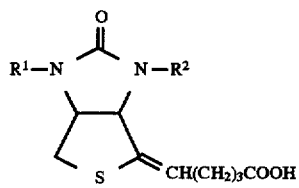
(3)

wherein $R^1$ and $R^2$ are each selected from the group consisting of an aralkyl group and allyl group, wherein said aralkyl group and allyl group are unsubstituted or substituted by one member selected from the group consisting of an alkyl group, alkoxyl group, nitro group, and halogen atom; wherein said process comprises the steps of:

(a) reacting a thienoimidazole represented by formula (1) with 1,4-dihalogenodimagnesium butane, in the presence of tetrahydrofuran or a mixed solvent comprising tetrahydrofuran and an aromatic solvent to produce a reaction mixture:

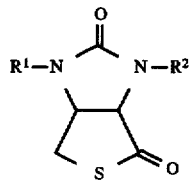
(1)

wherein $R^1$ and $R^2$ are as defined above; and wherein said thienoimidazole represented by formula (1) is added to said 1,4-dihalogenodimagnesium butane either directly or in a cake state or slurry state, wherein said cake state and slurry state are made by adding a small amount of either tetrahydrofuran or a mixed solvent comprising tetrahydrofuran and an aromatic solvent;

(b) reacting said reaction mixture obtained in step (a) with carbon dioxide to produce a reaction liquid; and (c) followed by hydrolyzing and dehydrating the reaction liquid.

13. The process according to claim 1, wherein at least one of said $R^1$ and $R^2$, in formula (1) and formula (2), is a benzyl group.

14. The process according to claim 7, wherein at least one of said $R^1$ and $R^2$, in formula (1) and formula (2), is a benzyl group.

15. The process according to claim 11, wherein at least one of said $R^1$ and $R^2$, in formula (1) and formula (3), is a benzyl group.

16. The process according to claim 12, wherein at least one of said $R^1$ and $R^2$, in formula (1) and formula (3), is a benzyl group.

* * * * *